(12) United States Patent
Shimura

(10) Patent No.: US 10,203,278 B2
(45) Date of Patent: Feb. 12, 2019

(54) FAR-INFRARED IMAGING DEVICE AND FAR-INFRARED IMAGING METHOD

(71) Applicant: Hitachi High-Technologies Corporation, Minato-ku, Tokyo (JP)

(72) Inventor: Kei Shimura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 212 days.

(21) Appl. No.: 15/100,441

(22) PCT Filed: Jan. 7, 2015

(86) PCT No.: PCT/JP2015/050198
§ 371 (c)(1),
(2) Date: May 31, 2016

(87) PCT Pub. No.: WO2015/122211
PCT Pub. Date: Aug. 20, 2015

(65) Prior Publication Data
US 2016/0299064 A1  Oct. 13, 2016

(30) Foreign Application Priority Data

Feb. 14, 2014  (JP) .................................. 2014-026037

(51) Int. Cl.
*G01N 21/3581*  (2014.01)
*G01J 1/42*  (2006.01)
(Continued)

(52) U.S. Cl.
CPC ........ *G01N 21/3581* (2013.01); *G01J 1/4228* (2013.01); *G01J 3/0205* (2013.01);
(Continued)

(58) Field of Classification Search
CPC .. G01N 21/3581; G01J 1/4228; G01J 3/0205; G01J 3/0224; G01J 3/108; G01J 3/2803; G01J 3/42; G01J 3/4338
See application file for complete search history.

(56) References Cited

U.S. PATENT DOCUMENTS 6,144,679 A * 11/2000 Herman ................ G02F 1/3534
250/495.1
6,388,799 B1 * 5/2002 Arnone .............. G01N 21/3581
359/326
(Continued)

FOREIGN PATENT DOCUMENTS

EP  2273254 A1 * 1/2011 .......... G01N 21/552
JP  2000-514549 A  10/2000
(Continued)

OTHER PUBLICATIONS

International Search Report (PCT/ISA/210) issued in PCT Application No. PCT/JP2015/050198 dated Mar. 24, 2015 with English translation (Two (2) pages).
(Continued)

*Primary Examiner* — David Porta
*Assistant Examiner* — Djura Malevic
(74) *Attorney, Agent, or Firm* — Crowell & Moring LLP

(57) ABSTRACT

Provided are an imaging method and device for imaging using far infrared light that make it possible to quickly image a subject without producing damage or a non-linear phenomenon in the subject. A variable-frequency coherent light source is used, illumination light from the light source is irradiated onto a linear area on an imaging subject, transmitted or reflected light is used to form an image of the imaging subject, a non-linear optical crystal is used for wavelength conversion, and a one-dimensional or two-dimensional array sensor is used to image the imaging
(Continued)

subject while the imaging subject is moved in at least one direction.

7 Claims, 6 Drawing Sheets

(51) Int. Cl.
*G01J 3/02* (2006.01)
*G01J 3/10* (2006.01)
*G01J 3/28* (2006.01)
*G01J 3/42* (2006.01)
*G01J 3/433* (2006.01)

(52) U.S. Cl.
CPC ........... *G01J 3/0208* (2013.01); *G01J 3/0224* (2013.01); *G01J 3/108* (2013.01); *G01J 3/2803* (2013.01); *G01J 3/42* (2013.01); *G01J 3/4338* (2013.01)

(56) References Cited

U.S. PATENT DOCUMENTS

| | | | | |
|---|---|---|---|---|
| 8,742,353 | B2* | 6/2014 | Kawada | G01N 21/35 250/338.4 |
| 8,993,967 | B2* | 3/2015 | Kawada | G01N 21/21 250/353 |
| 2002/0024718 | A1* | 2/2002 | Kawase | G02F 1/39 359/330 |
| 2003/0227668 | A1* | 12/2003 | Imai | G02F 1/39 359/326 |
| 2007/0152154 | A1* | 7/2007 | DeCamp | G01J 3/2803 250/339.07 |
| 2007/0195921 | A1 | 8/2007 | Ouchi | |
| 2008/0225383 | A1* | 9/2008 | Theberge | G02F 1/3511 359/326 |
| 2010/0090112 | A1* | 4/2010 | Kawada | G01N 21/3581 250/338.4 |
| 2011/0057109 | A1 | 3/2011 | Guo et al. | |
| 2013/0088590 | A1 | 4/2013 | Shimura et al. | |

FOREIGN PATENT DOCUMENTS

| | | |
|---|---|---|
| JP | 2003-75251 A | 3/2003 |
| JP | 2004-85359 A | 3/2004 |
| JP | 2007-218661 A | 8/2007 |
| JP | 2008-96210 A | 4/2008 |
| JP | 2009-122007 A | 6/2009 |
| JP | 2011-75583 A | 4/2011 |
| JP | 2012-26943 A | 2/2012 |
| WO | WO 97/45747 A1 | 12/1997 |
| WO | WO 2006/085403 A1 | 8/2006 |
| WO | WO 2006/088802 A2 | 8/2006 |
| WO | WO 2011/094564 A2 | 8/2011 |

OTHER PUBLICATIONS

Japanese-language Written Opinion (PCT/ISA/237) issued in PCT Application No. PCT/JP2015/050198 dated Mar. 24, 2015 (Four(4) pages).

Handbook of Terahertz Technology edited by Terahertz Technology Forum, Nov. 29, 2007, NGT Corp., pp. 426-456 (Seventeen (17) pages).

Shikata, J., et al., "THz-Wave Parametric Generation and Its Linewidth Control", The Institute of Electronics, Information and Communication engineers Transations C, vol. J85-C, No. 2, Feb. 2002, pp. 52-63 (Twelve (12) pages).

Hayashi, S., et al., "High-peak-power and Tunable Terahertz-wave Generation and Sensitive Detection by Using Nonlinear Parametric Conversion", Proc. of $37^{th}$ International Conference on Infrared, Millimeter, and Terahertz Waves (IRMMW-THz), Mon-B-1-2, Sep. 24, 2012 (Three (3) pages).

Herrmann, M., et al., "Multi-channel Signal Recording with Photoconductive Antennas for Thz Imaging", 2002, Proc. of $10^{th}$ IEEE International Conference on Thz Electronics (THz2002), pp. 28-31, (Four (4) pages).

Third party submission of opinion and/or information issued in counterpart Japanese Application No. 2014-026037 dated Jan. 10, 2017 with English-language translation (seventeen (17) pages).

Extended European Search Report issued in counterpart European Patent Application No. 15748745.5 dated Sep. 14, 2017 (three (3) pages).

Clerici, M. et al, "CCD-based Imaging and 3D Space-Time Mapping of Terahertz Fields via Kerr Frequency Conversion," Optics Letters, Optical Society of America, vol. 38, No. 11, Jun. 1, 2013, pp. 1899-1901, XP-001582929.

* cited by examiner

FAR-INFRARED IMAGING DEVICE AND FAR-INFRARED IMAGING METHOD

TECHNICAL FIELD

The present invention relates to a far-infrared imaging apparatus for capturing an image of a specimen by using light in a far-infrared region in testing steps such as analysis of component distribution of chemical substances in a specimen or testing of a different component or a foreign substance and relates to an imaging method using the same.

BACKGROUND ART

Electromagnetic waves in a far-infrared region from about 25 μm to 4 mm in wavelength are also referred to as terahertz waves and have both transmittance of a radio wave and straightness of light, and many substances have inherent peaks in absorption spectra in this region. Therefore, the electromagnetic waves are expected to be effective in identifying substances. However, conventionally, there have been no small and easy-to-use light sources for emitting light in this region, and a detector therefor needs to be cooled by liquid helium or the like and is therefore difficult to handle. Thus, the electromagnetic waves have been used only for limited research use.

In 1990s, light sources and detectors using femtosecond lasers, which have a small size and do not need to be cooled, were implemented, and research and development for implementation thereof have been eagerly performed. At present, general-purpose spectrometry devices based on time-domain spectroscopy are commercially available, and research and development are being performed for application to various fields such as security, biosensing, medical/pharmaceutical, industrial, and agricultural fields (for example, see NPL 1). Since about 2000, compact coherent light sources capable of tuning a frequency in a broad band have also been eagerly researched, which causes increase in power thereof (for example, see NPL 2). Furthermore, a technique for performing detection using a non-linear optical crystal at high SN has also been developed (for example, see NPL 3).

For industrial application, it is required to acquire an image of a specimen in many fields. As means for achieving this, there has conventionally been known a method of acquiring an image by placing a specimen on an XY stage and repeatedly measuring the specimen while moving the specimen by using a spectroscopic analysis device for point detection (for example, see NPL 1). Further, a method using a two-dimensional array far-infrared light detector (for example, see PTL 1) and a method of acquiring an image by using an electrooptical crystal and a two-dimensional array CCD camera for visible light (for example, see PTL 2) are also proposed. Furthermore, a method using a one-dimensional array far-infrared light detector is also proposed (for example, see NPL 4).

CITATION LIST

Patent Literatures

PTL 1: JP Patent Publication (Kokai) 2003-075251 A
PTL 2: JP Patent Publication (Kohyo) 2000-514549 A1

Non Patent Literatures

NPL 1: Handbook of Terahertz Technology edited by Terahertz Technology Forum, pp. 426-456, published by NGT corporation on Nov. 29, 2007

NPL 2: Shikata et. al THz-Wave Parametric Generation and Its Linewidth Control, the Institute of Electronics, information and Communication Engineers Transactions C, Vol. J85-C, No. 2, pp. 52-63 (2002)

NPL 3: S, Hayashi. et, al., "High-peak-power and tunable terahertz-wave generation and sensitive detection by using nonlinear parametric conversion", Proc. of 37th International Conference on Infrared, Millimeter, and Terahertz Waves (IRMMW-THz), Mon-B-1-2, September 24 (2012)

NPL 4: Michael Herrmann et. al., "Multi-channel Signal Recording with Photoconductive Antennas for THz Imaging", Proc. of 10th IEEE International Conference on THz Electronics (THz2002), pp. 28-31 (2002)

SUMMARY OF INVENTION

Technical Problem

For industrial application, testing of many specimens and testing of a large specimen are demanded, and therefore speedy image acquisition is required. However, in a method based on conventional point measurement, in which an image is formed by moving a specimen in X and Y directions, it takes a few hours to acquire one image in some cases. This is a cause of delaying implementation.

For speeding-up, it is necessary to use a high-power light source to irradiate a measurement point, with larger optical energy to thereby reduce a measurement time for each point and speed up scanning in the X and Y directions. However, when a measurement point is irradiated with high-power light in point measurement, the specimen may be damaged due to heat generated by absorption of optical energy or a non-linear effect may be exerted due to electric field intensity of light, and therefore a measurement result may be changed.

Meanwhile, the method using a two-dimensional array detector is suitable for speeding-up because scanning of a specimen in the X and Y directions is unnecessary or frequency thereof can be remarkably reduced. However, the methods needs to irradiate a large area while maintaining illuminance of illumination light, which requires a much higher-power light source. In the case where the power of the light source is insufficient, an exposure time to acquire an image at one position becomes long and a sufficient speeding-up effect cannot be exerted.

In the case where the light source using a femtosecond laser is used, it is necessary to acquire various data while changing an optical path length of detection light in order to acquire spectrometry measurement data for one point. Therefore, it takes time for measurement even in the case where a high-power light source and a two-dimensional array detector are used.

An object of the invention is to provide an imaging method and an imaging apparatus which can perform imaging at a high speed in imaging using far-infrared light without causing damage to or a non-linear phenomenon in a specimen serving as an imaging target.

Solution to Problem

In order to achieve the above object, in the invention, a frequency-tunable coherent light source having higher power is used, and a line on an imaging target is irradiated with illumination light from a light source by using an illumination optical system, an image of the imaging target is formed by using transmitted light or reflected light, wavelength conversion is performed by using a non-linear optical crystal, the imaging target is imaged by using a one-dimensional or two-dimensional array sensor while being moved in at least one direction.

Advantageous Effects of Invention

According to the invention, it is possible to perform imaging at a high speed by using a high-power light source without causing damage to or a non-linear Phenomenon in a specimen serving as an imaging target.

DESCRIPTION OF EMBODIMENTS

Hereinafter, examples of the invention will be described with reference to the attached drawings.

Example 1

Figure 1:
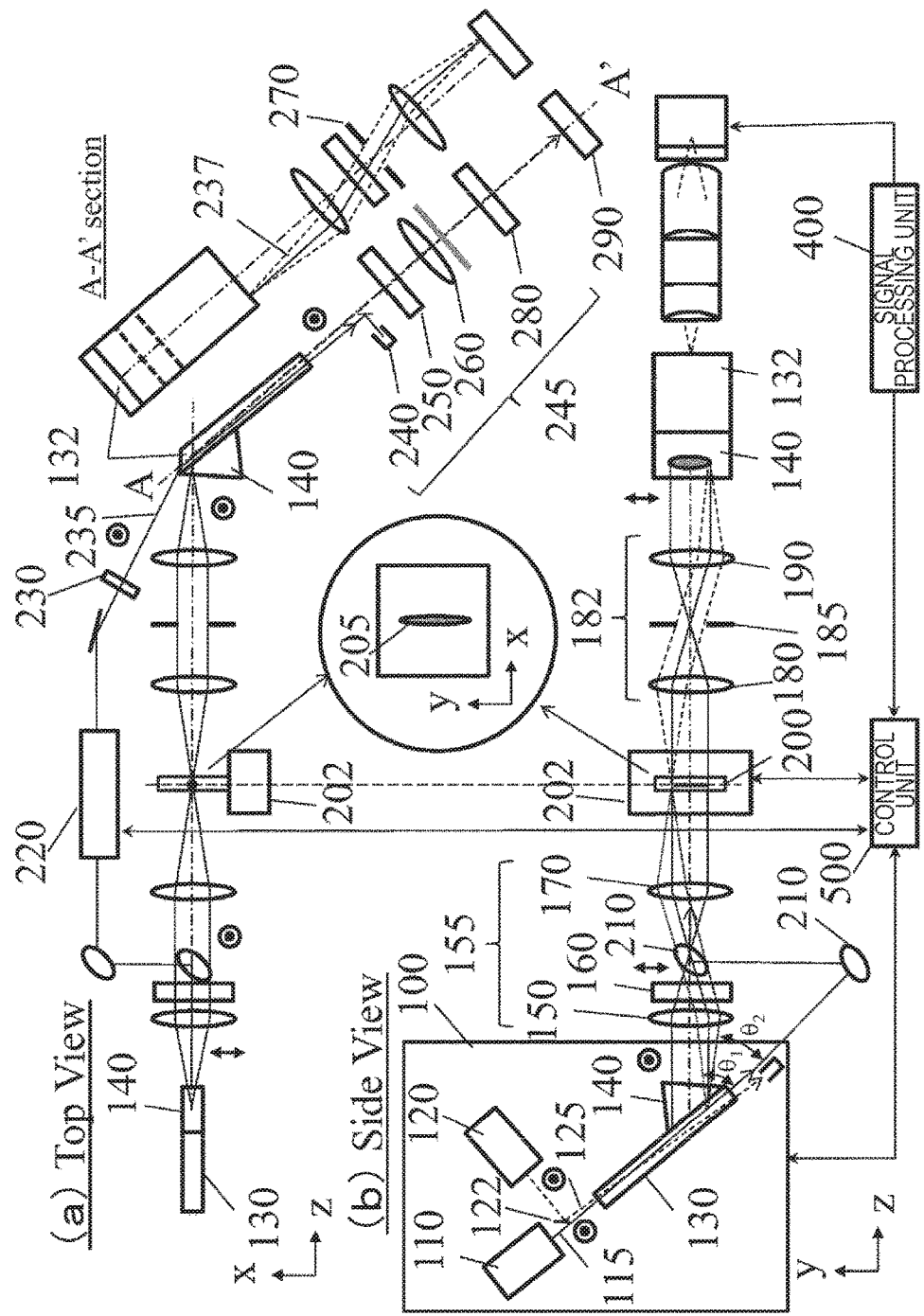
FIG. 1 illustrates a configuration example of an imaging apparatus using light in a far-infrared region in Example 1.

FIG. 1 illustrates an example of the whole configuration of an imaging apparatus in Example 1. FIG. 1 illustrates a configuration example of an apparatus for imaging an image of a specimen 200 by using light transmitted through the specimen 200. This apparatus includes a wavelength-tunable far-infrared light source 100, an illumination optical system 155, a stage 202, a far-infrared light imaging optical system 182, a non-linear optical crystal 132 for detection, a detection optical system 245, a light detector 290, a pump light irradiation optical system 220, a control unit 500, and a signal processing unit 400.

As the wavelength-tunable far-infrared light source 100, there is used a far-infrared light source for generating far-infrared light due to difference frequency generation or parametric generation by causing two kinds of laser beams having different wavelengths to enter a non-linear optical crystal. For example, when MgO:LiNbO3 is used as a non-linear optical crystal 130, a Q-switch YAG laser with a short pulse is used as a light source 110 of pump light 115, and light from a wavelength-tunable light source 120 is caused to enter the non-linear optical crystal 130 as seed light 125, it is possible to obtain far-infrared light due to parametric generation. When a Si prism 140 is attached to the non-linear optical crystal 130, it is possible to efficiently extract the generated far-infrared light. When a wavelength of the seed light 125 is changed between about 1066 nm to 1076 nm and an incident angle thereof to the non-linear optical crystal 130 is adjusted, it is possible to change a frequency of the generated far-infrared light in a range from about 0.5 THz to 3 THz.

A linear illumination region 205 on the specimen 200 is irradiated with the far-infrared light obtained as described above by using the illumination optical system 155. As the illumination optical system 155, an imaging optical system including at least two lenses 150 and 170 is used. Specifically, a light source of far-infrared light is arranged in a front focal plane of the lens 150, and the lens 170 is arranged so that a rear focal plane of the lens 150 and a front focal plane of the lens 170 correspond to each other, and further the specimen 200 is arranged in a rear focal plane of the lens 170. When an aperture stop is provided in the rear focal plane of the lens 150 (that is, which is also the front focal plane of the lens 170), a double telecentric optical system is formed, but the aperture stop is not essential herein. Far-infrared light emitted from the wavelength-tunable far-infrared light source 100 is a beam-like light source along beams of the pump light 115 and is diverged in FIG. 1(a) and is a parallel luminous flux in FIG. 1(b). In FIG. 1(a), light is converted into a parallel luminous flux by the lens 150 and is converged on the line of the specimen through a polarization rotation optical element 160 for rotating a polarization direction of far-infrared light at 90 degrees and the lens 170. Meanwhile, in FIG. 1(b), light is concentrated by the lens 150 once, is transmitted through the polarization rotation optical element 160 for rotating a polarization direction of far-infrared light at 90 degrees, and then becomes a parallel luminous flux at the lens 170 again, and thus the specimen is irradiated with the light. When the illumination optical system is an afocal system (that is, the lens 170 is arranged so that the rear focal plane of the lens 150 and the front focal plane of the lens 170 correspond to each other), it is possible to irradiate the specimen 200 with substantially parallel far-infrared light in FIG. 1(b), which is generated in the non-linear optical crystal 130, as a parallel luminous flux as it is. This makes it possible to efficiently introduce far-infrared light transmitted through the specimen into the far-infrared light imaging optical system 182.

Because the illumination optical system 155 is the imaging optical system as described above, it is possible to obtain stability of illumination when a wavelength of far-infrared light emitted from the wavelength-tunable far-infrared light source 100 is changed. In order to change the wavelength of the far-infrared light, the incident angle is adjusted by changing the wavelength of the seed light 125. However, in that case, an emission direction of generated far-infrared light changes in an in-plane direction of FIG. 1(b) (for example, θ1 to θ2 in FIG. 1). When the illumination optical system 155 is the imaging optical system and a light source of far-infrared light and a surface of the specimen 200 have a conjugate relationship (imaging relationship), it is possible to prevent a spot of far-infrared light from moving even on the surface of the specimen 200. Because a position is not changed even in the case where a wavelength of far-infrared light is changed, an illumination light amount is also not changed, and therefore stable illumination can be obtained. On the contrary, in the case where the illumination optical system 155 is not an imaging optical system, an illumination position of illumination light may be shifted to a completely different position, and therefore stable imaging is difficult. However, this shall not apply where imaging is performed at a fixed wavelength or Where a wavelength is changed in a small range and a change in a direction of far-infrared light is sufficiently small.

The polarization rotation optical element 160 converts a polarization plane of far-infrared light that is emitted from the Si prism 140 and vibrates in a direction (x direction) vertical to the sheet of FIG. 1(b) into polarized light that vibrates in a y direction in the sheet of FIG. 1(b). Herein, the reason why the polarization plane is rotated is that a polarization direction of far-infrared light to be incident on the non-linear optical crystal 132 for detection is changed to a direction needed for detection in accordance with a direction of the non-linear optical crystal 132. In the case where a wavelength of far-infrared light is changed in a wide range, a polarization rotation system having low wavelength dependency, such as an achromatic wave plate, is needed. In the case there the wavelength is changed in a narrow range and wavelength dependency of polarization rotation performance is ignorable, a half-wave plate using birefringence of quartz is preferably used as the polarization rotation element 160. Because a phase difference is used, the wavelength dependency remains in the polarization rotation performance, but a size of the optical system can be reduced.

The specimen 200 serving as an imaging target is placed on the stage 202 and is movable in at least one direction. When data of the line is acquired while the specimen 200 is being moved in a direction (x direction) orthogonal to a longitudinal direction of the linear illumination region 205, it is possible to acquire data (image) of the surface of the specimen 200. In the case where a region to be imaged on the specimen 200 is longer than a length of the linear illumination region 205 in the longitudinal direction, an xy stage is used as the stage 202 to combine scanning in the x direction with feeding in the y direction, and therefore imaging can be performed in a wider region.

Detection of far-infrared light transmitted through the specimen 200 is performed by performing wavelength conversion in the non-linear optical crystal 132 from far-infrared light into near-infrared light having a wavelength of around 1066 nm to 1076 nm, introducing the near-infrared light into the light detector 290 by using the detection optical system 245, and performing photoelectric conversion in the light detector 290 having sensitivity to near-infrared light. As a near-infrared detector, a 1D or 2D array detector is suitable for industrial application because the array detector is comparatively easily available, has a high response speed, and can be used at a room temperature.

Far-infrared light transmitted through the specimen 200 is introduced into the non-linear optical crystal 132 for detection by using the far-infrared light imaging optical system 182. The far-infrared light imaging optical system 182 is a double telecentric imaging optical system including at least two lenses 180 and 190 and an aperture stop 185 and forms an image of the surface of the specimen 200 in the non-linear optical crystal 132 through the Si prism 140. On the surface of the specimen 200, the linear region 205 is irradiated with far-infrared light, and therefore this part is imaged on a line in the non-linear optical crystal 132. As the non-linear optical crystal 132, $LiNbO_3$ or $MgO:LiNbO_3$ is preferably used.

Figure 2:
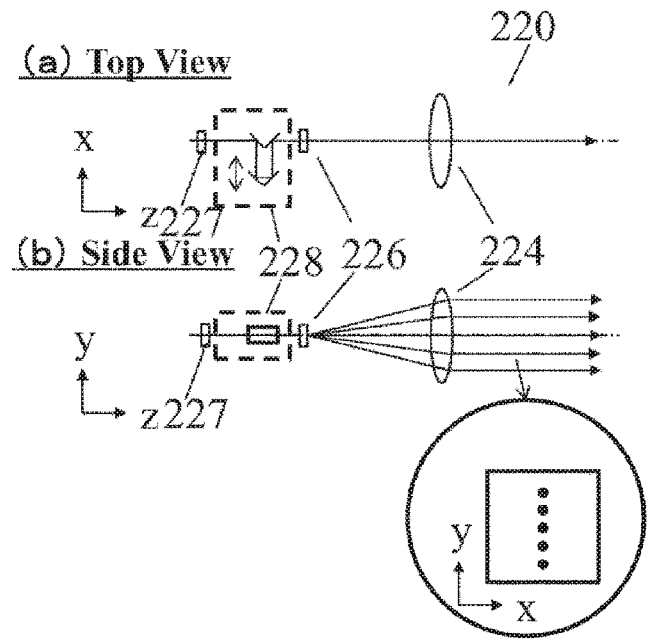
FIG. 2 illustrates an example of a pump beam shaping optical system for detection in Example 1.
Figure 8:
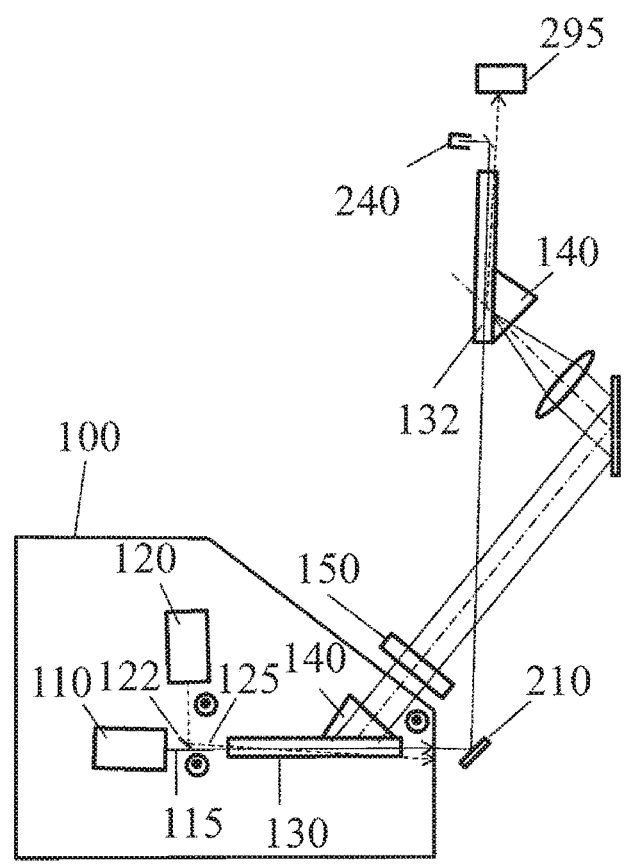
FIG. 8 illustrates a configuration example of an imaging apparatus using light in a far-infrared region (conventional example).

As pump light 235 needed for wavelength conversion, pump light used for generating far-infrared light in the wavelength-tunable far-infrared light source 100 is incident on the non-linear optical crystal 132 through the pump light irradiation optical system 220 and a half-wave plate 230. As illustrated in FIG. 2, the pump light irradiation optical system 220 includes a half-wave plate 227, a delay optical system 228 for matching a timing of a light pulse, a diffractive optical element 226 for dividing a beam into a plurality of beams, and a lens 224 for restoring the divided beams to a line of parallel beams. Each of the divided beams is a pump light beam for detection for use in a single channel detection system in a conventional example illustrated in FIG. 8. The divided beams are adjusted by the half-wave plate 230 so that a polarization direction thereof corresponds to an axis direction of the non-linear optical crystal 132 (y axis direction in FIG. 1) and are introduced into the non-linear optical crystal 132.

Figure 3:
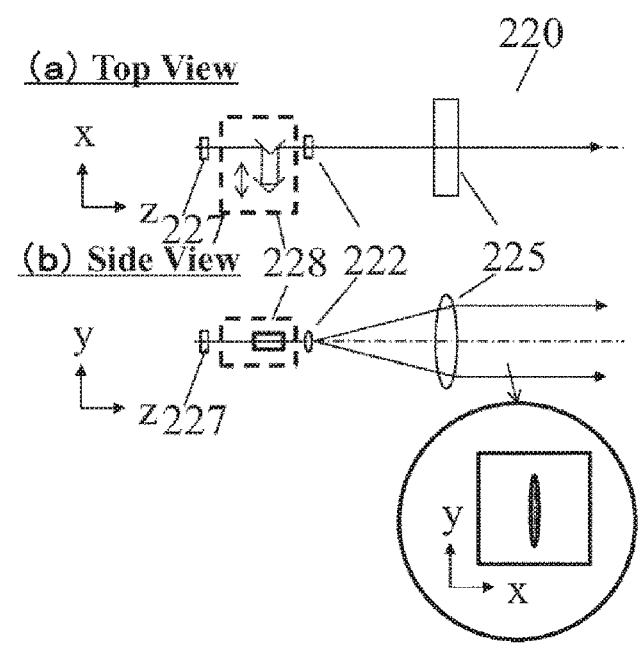
FIG. 3 illustrates a second example of the pump beam shaping optical system for detection in Example 1.

FIG. 3 illustrates another example of the pump light irradiation optical system 220. FIG. 3 is different from FIG. 2 in that beams are enlarged in one direction to form elliptical beams by using a cylindrical lens 222 instead of the diffractive optical element 226 for dividing a beam into a plurality of beams and using a cylindrical lens 225 instead of the lens 224 for restoring the beams to a line of parallel beams. Pump light is formed into not isolated beams but continuous beams, and therefore it is expected that near-infrared light subjected to wavelength conversion is also continuous. This makes it possible to achieve detection with high lateral resolution.

Note that, herein, an example where the half-wave plate 227 is arranged in the pump light irradiation optical system 220 and the half-wave plate 230 is arranged behind the pump light irradiation optical system 220 has been described, but any one of the half-wave plates may be omitted. When both the half-wave plates are used, a degree of freedom in design of an optical system layout can be high. However, in the case where a certain layout taken into consideration of restriction of a polarization direction can be employed, any one of the half-wave plates can be omitted. Because the half-wave plate 227 of the pump light irradiation optical system 220 is arranged before a beam is divided, it is possible to use a half-wave plate having a small effective aperture. In the case where the half-wave plate 230 is arranged behind the pump light irradiation optical system 220, a polarization direction thereof is not disrupted because no optical element is provided therebehind, and therefore it is possible to introduce pump light having optimal polarization into the non-linear optical crystal 132.

Herein, an example where pump light used for generating far-infrared light in the wavelength-tunable far-infrared light source 100 is reused as the pump light 235 needed for wavelength conversion has been described. However, in the case where the power of the light source 110 of the pump light is sufficient, the pump light 115 may be divided into two parts in front of the non-linear optical crystal 130, and one part may be used to generate far-infrared light and the other part may be used to perform wavelength conversion at the time of detection. With this, beams having a clear profile can be used to perform wavelength conversion at the time of detection. This makes it possible to improve efficiency of wavelength conversion and improve detection sensitivity.

Figure 4:
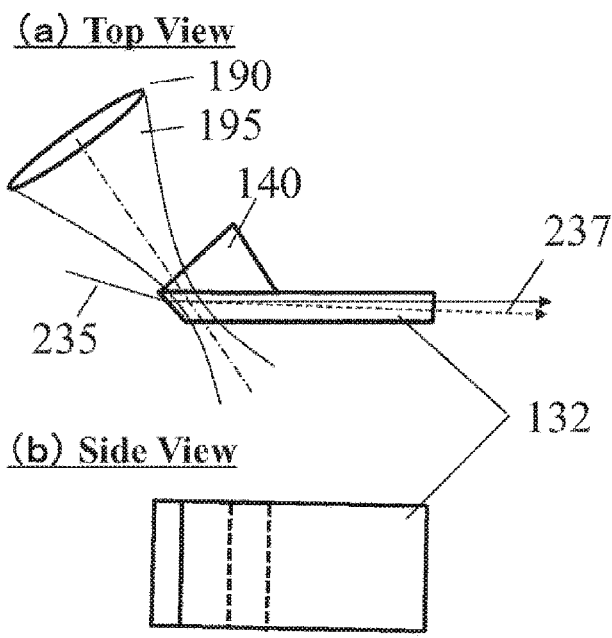
FIG. 4 illustrates an example of a non-linear crystal for detection in Example 1.
Figure 5:
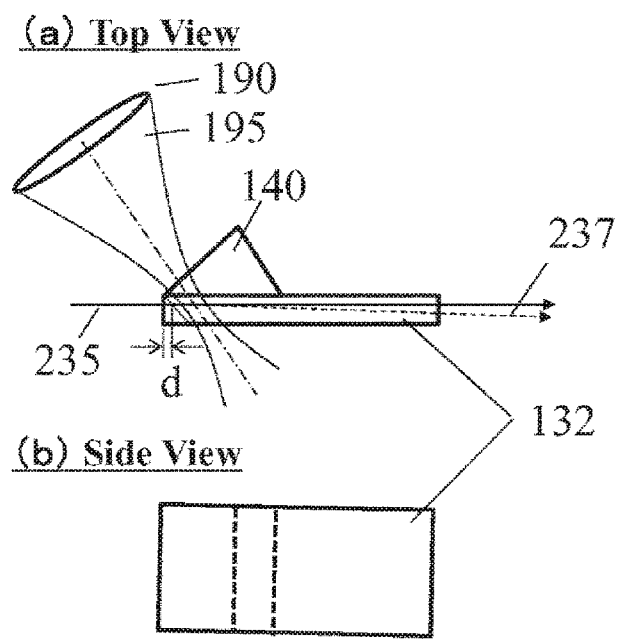
FIG. 5 illustrates a configuration example of a non-linear crystal for detection (conventional example).

FIG. 4 illustrates an example of the non-linear optical crystal 132 for detection used in this example. FIG. 5 illustrates an example of the conventional non-linear optical crystal 132 for comparison. The Si prism 140 is provided on the nonlinear optical crystal 132, and far-infrared light 195 transmitted through the specimen 200 is incident therethrough. The pump light 235, which is obtained by shaping beams into elliptical beams or a line of isolated beams in the pump light irradiation optical system 220, is introduced into the crystal through an end surface of the non-linear optical crystal 132. Wavelength conversion occurs due to interaction of those two kinds of beams, and near-infrared light 237 corresponding to a wavelength of the far-infrared light incident thereon is emitted from the end surface of the crystal. In this example, as the nonlinear optical crystal 132, a crystal that causes an incident end of the pump light 235 to be in parallel to an incident optical axis of the far-infrared light 195 is used. Because such a shape is employed, it is possible to reduce a region where the pump light 235 exists and far-infrared light does not exist in the crystal. Generally, when intensive pump light is incident on the non-linear optical crystal, light having a wavelength different from that of the pump light is spontaneously emitted from atoms excited by the pump light even in the case where far-infrared light does not exist, and the light is amplified to be detected as a light noise in some cases. In the conventional example (FIG. 5), a part of a distance d along an optical path of the pump light 235 is a noise source. This unnecessary part of the crystal which can be a noise source is reduced in this example, and therefore it is possible to reduce noise components and detect far-infrared light signals at high SN. Note that inclination of a surface of the incident end of the nonlinear optical crystal 132 does not need to be strictly in parallel to the incident optical axis of the far-infrared light 195. It is only necessary that a region where the pump light 235 exists and far-infrared light does not exist in the crystal can be substantially reduced. In this example, it is necessary to propagate the pump light 235 in substantially parallel to upper and lower surfaces of the nonlinear optical crystal 132 in FIG. 4(a), and therefore, in this example, it is preferable to cause the pump light 235 to be obliquely incident on the upper and lower surfaces of the nonlinear optical crystal 132 in consideration of refraction on an incident surface thereof.

Near-infrared light generated by wavelength conversion in the non-linear optical crystal 132 is formed into elliptical beams or a line of isolated beams depending on a shape of the pump light 235 for detection. Those beams are introduced into the light detector 290 by the detection optical system 245 in which two orthogonal cross sections passing through an optical axis have different imaging relationships.

The detection optical system 245 is preferably configured so that at least the non-linear optical crystal 132 side is telecentric in an A-A' section of FIG. 1(a) (that is, cross section along linear illumination) and beams of near-infrared light generated by wavelength conversion are concentrated on the light detector 290 in the plane of FIG. 1(a) (that is, cross section orthogonal to linear illumination) orthogonal to the A-A' section. FIG. 1 illustrates the example where the A-A' section is double telecentric, and the example is preferably configured by using cylindrical lenses 250 and 280 and an aperture stop 270 as illustrated in FIG. 1. In FIG. 1(a), beams only need to be simply concentrated on the light detector 290, and therefore it is only necessary that the cylindrical lens 260 is provided and the light detector 290 is arranged in the vicinity of a focal plane thereof. The near-infrared light 237 generated by wavelength conversion, which is illustrated in the A-A' section of FIG. 1(a), is an example of a luminous flux of near-infrared light emitted from one point deviating from the optical axis. This near-infrared light travels in parallel to the optical axis along the pump light 235 in the A-A' section, and therefore it is possible to efficiently introduce the near-infrared light into the light detector 290 by forming the detection optical system 245 so that the non-linear optical crystal 132 side is telecentric. Further, stray light is blocked by the aperture stop 270, and therefore it is possible to detect near-infrared light at a high SN ratio. Note that the remainder of the pump light 235 is also emitted from an emission end of the non-linear optical crystal 132. Because light intensity thereof is high, it is desired to appropriately perform termination processing by using a beam dump 240 so as to prevent the remainder of the pump light from becoming stray light.

As the light detector 290, a one-dimensional array or two-dimensional array having sensitivity to a wavelength of about 1066 nm to 1076 nm is used. A back-illuminated CCD sensor made of Si or an InGaAs sensor is preferably used.

In the configuration in this example, in the case where a wavelength of far-infrared light is changed, a spot of near-infrared light emitted from the non-linear optical crystal 132 and concentrated on the light detector 290 moves in an in-plane direction in FIG. 1(a) depending on the wavelength of the far-infrared light. Therefore, when a two-dimensional array sensor is used as the light detector 290, it is possible to measure a wavelength of far-infrared light detected from a spot position, and therefore an absorption spectrum can be accurately measured. Meanwhile, in the case where measurement of the wavelength is unnecessary, a one-dimensional array sensor may be used, in this case, the one-dimensional array sensor is arranged so that pixels are arrayed in the A-A' section of FIG. 1(a). The pixels are arranged in a direction corresponding to the longitudinal direction of the linear illumination region 205 on the specimen 200, and therefore it is possible to image the linear illumination region 205 at once. Note that, in order that the linear illumination region is within a region of the pixels even in the case where the spot moves, it is preferable to use a one-dimensional array sensor having wide pixels whose pixel width in a direction orthogonal to a pixel array is larger than a pixel pitch. When the one-dimensional array sensor is used, an amount of information output from the sensor is reduced to reduce information processing, and therefore it is possible to perform processing at a high speed or processing in a simple circuit.

Note that the detection optical system 245 may be configured so that at least the non-linear optical crystal 132 side is telecentric in the A-A' section of FIG. 1(a) (that is, cross section along linear illumination) and may be a simple imaging optical system in the plane of FIG. 1(a) (that is, cross section orthogonal to linear illumination) orthogonal to the A-A' section. This can be achieved by only arranging the cylindrical lens 260 so that an emission surface of the non-linear optical crystal 132 and a surface of the light detector 290 have an imaging relationship in the configuration illustrated in FIG. 1. When an emission end surface of the non-linear optical crystal 132 is imaged on the surface of the light detector 290 in the FIG. 1(a), it is possible to fix near-infrared light emitted from the non-linear optical crystal 132 in the same position of the light detector 290 even in the case where a wavelength of far-infrared light is changed. Therefore, it is possible to form a simple system by using a one-dimensional array sensor as the light detector 290. Further, an amount of information output from the sensor is reduced to reduce information processing, and therefore it is possible to perform processing at a high speed or processing in a simple circuit.

The control unit 500 controls the whole apparatus and functions as a user interface. The control unit 500 controls the wavelength-tunable far-infrared light source 100, the stage 202, the pump light irradiation optical system 220, and the signal processing unit 400 and displays signals and data processed in the signal processing unit 400. In the case where imaging is performed while a wavelength is being fixed, the wavelength-tunable far-infrared light source 100 is controlled to generate specified far-infrared light, and synchronization between move of the stage 202 and data acquisition in the light detector 290 is control led. In the case where data is acquired while a wavelength is being changed, setting of the wavelength and synchronization between move of the stage 202 and data acquisition in the light detector 290 are controlled. Further, when an optical path length in the delay optical system 228 of the pump light irradiation optical system 220 is controlled depending on a thickness of the specimen 200 and a timing of the far-infrared light 195 transmitted through the specimen 200 is matched with a timing of the pump light 235, it is possible to achieve detection at high SN.

The signal processing unit 400 receives a signal subjected to photoelectric conversion in the light detector 290 and generates an image of the specimen 200 on the basis of positional information on the stage 202 obtained at the time of receiving the signal. In the case where a one-dimensional array sensor is used as the light detector 290, wavelength information specified by the wavelength-tunable far-infrared light source 100 is integrated, and therefore an image for each wavelength or an image obtained by integrating spectroscopic information is generated. In the case where a two-dimensional array sensor is used as the light detector 290, wavelength information on illumination light and information on transmittance or reflectance of the specimen 200 corresponding thereto are extracted from output data from the light detector 290, and therefore an image for each wavelength or an image obtained by integrating spectroscopic information is generated. By comparing the above image with spectroscopic image data (reference data) obtained when no specimen is placed, the spectroscopic image data being stored in a storage area of the signal processing unit 400, an absorption spectrum is calculated, and therefore two-dimensional distribution (absorption spectrum image) of the absorption spectrum can be obtained.

Note that, in this example, an example where a Q-switch YAG laser with a short pulse is used as the light source 110 of the pump light 115 of the wavelength-tunable far-infrared light source 100 has been described. However, a line width of a basic spectrum only needs to be small, and therefore a mode-locked laser may be used. Because a repetition rate thereof is high, it is possible to perform measurement at a higher speed.

Example 2

Figure 6:
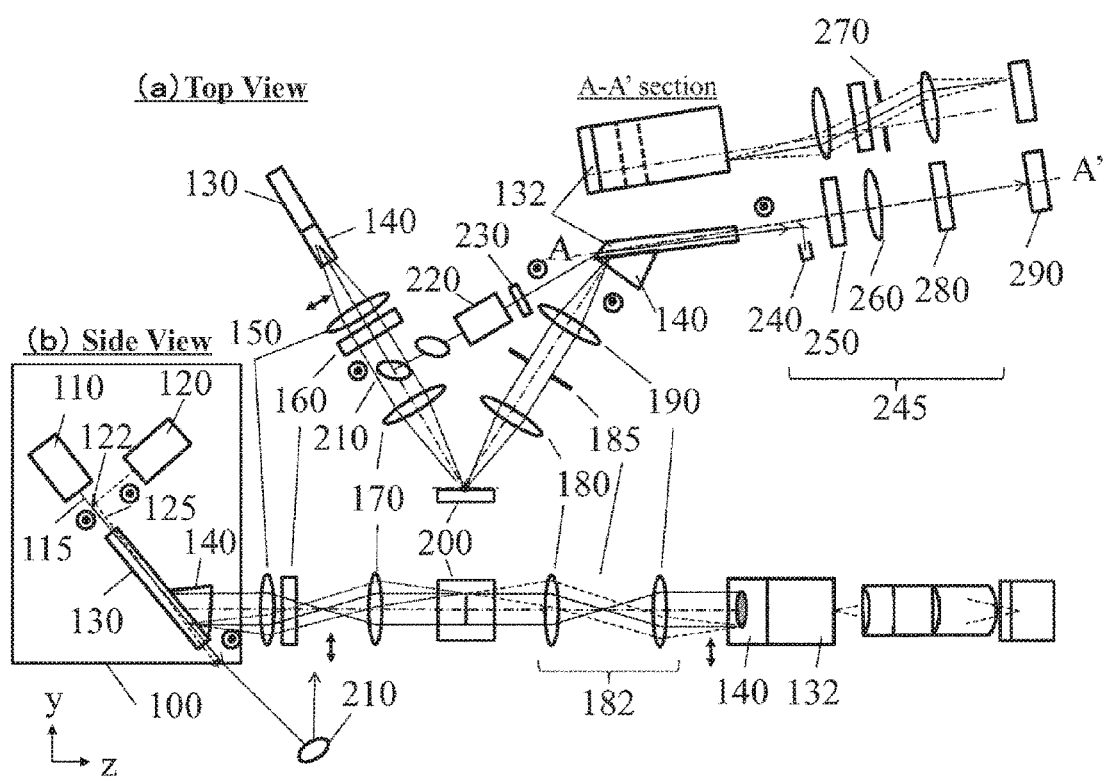
FIG. 6 illustrates a configuration example of an imaging apparatus using light in a far-infrared region in Example 2.

FIG. 6 illustrates a configuration example of an imaging apparatus in Example 2. In this configuration, imaging is performed by using reflected light of the specimen 200. The directions of the optical path from the wavelength-tunable far-infrared light source 100 to the illumination optical system 155 and the optical path from the far-infrared imaging optical system 182 and thereafter are changed at the surface of the specimen 200, far-infrared light is caused to be obliquely incident on the specimen 200 and reflected light thereof is detected. With this, it is possible to measure a specimen having low transmittance and measure a spectroscopic property of a surface of the specimen. When a mechanism system capable of changing incident angles of an illumination system and an imaging optical system is constructed, incident angle dependency of the spectroscopic property can be also measured.

Example 3

Figure 7:
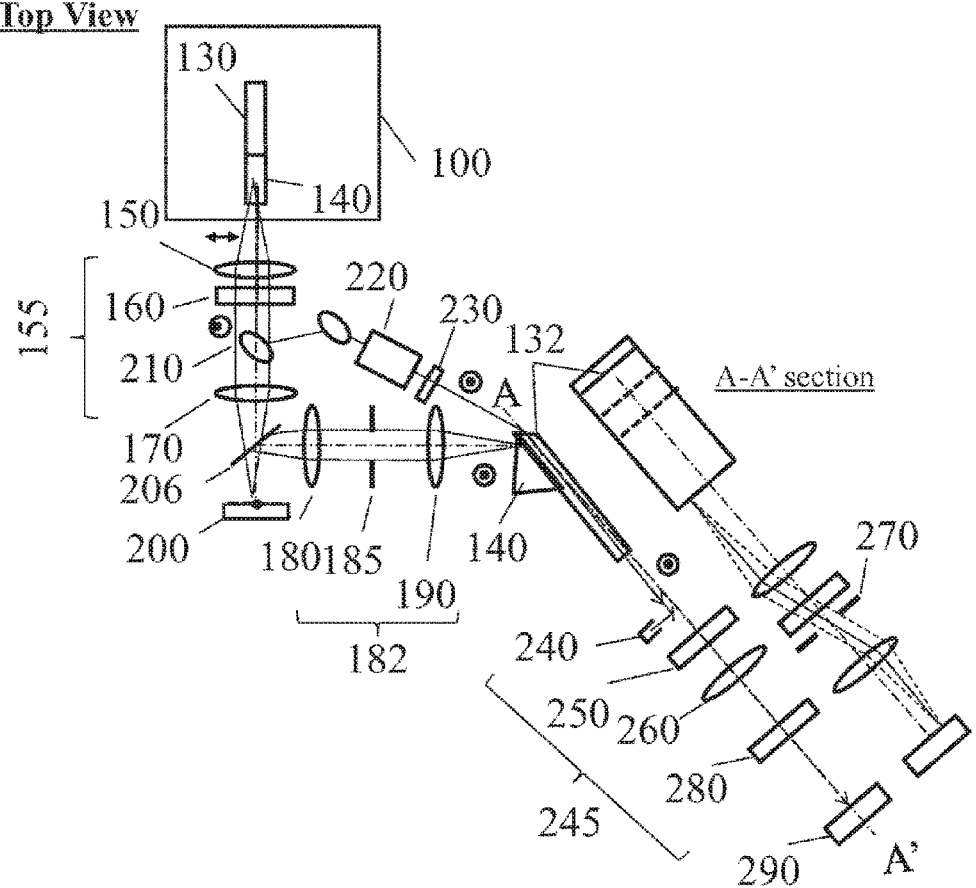
FIG. 7 illustrates a configuration example of an imaging apparatus using light in a far-infrared region in Example 3 (Example 3).

FIG. 7 illustrates a configuration example of an imaging apparatus in Example 3. In this configuration, imaging is performed by causing far-infrared light to be vertically incident on the specimen 200 and using reflected light thereof. When the wavelength-tunable far-infrared light source 100 to the illumination optical system 155 and the far-infrared imaging optical system 182 and thereafter are overlapped by a beam splitter 206 around the surface of the specimen 200, far-infrared light is caused to be vertically incident on the specimen 200 and reflected light thereof is detected. In the case where a polarization beam splitter is used as the beam splitter 206, it is possible to omit the polarization rotation optical element 160. Further, it is also possible to form a system for polarizing and separating incident light and reflected light by using a polarization beam splitter as the beam splitter 206 and providing a quarter-wave plate therebehind. With this, even in the case Where a specimen has large incident angle dependency of a spectroscopic property, it is possible to measure a basic property thereof without considering the incident angle dependency.

Note that, in this example, there has been described an example where the linear illumination region 205 on the specimen 200 is irradiated with far-infrared light by using the illumination optical system 155 and detection is performed by using a line of isolated beams as pump light for detection in order to perform imaging. However, a part of the linear illumination region 205, which is a region where no specimen exists, may be irradiated to acquire reference data for absorbance measurement. It is possible to simultaneously acquire the reference data and light transmitted through a specimen or reflected light thereof, and therefore it is possible to reduce an influence of disturbances such as a change in output of a laser light source and an electric noise entering a circuit of a detection system. Thus, measurement can be achieved with high accuracy.

REFERENCE SIGNS LIST 100 wavelength-tunable far-infrared light source
200 specimen
155 illumination optical system
205 linear illumination region
182 far-infrared light imaging optical system
185, 270 aperture stop
235, 115 pump light
130, 132 non-linear optical crystal
245 detection optical system
290 light detector, array sensor
202 stage
110, 120 laser light source
115, 125 laser beam
140 Si prism
160 polarization rotation element
270 pump light irradiate optical system
226 diffractive optical element
227, 230 half-wave plate

The invention claimed is:
1. A far-infrared imaging apparatus, comprising:
a wavelength-tunable far-infrared light source;
an illumination optical system for irradiating a specimen with far-infrared light;
a far-infrared light imaging optical system for forming an image of the specimen;
a non-linear optical crystal for detection being arranged in the vicinity of an image plane of the far-infrared light imaging optical system;
an array sensor;

a detection optical system for introducing light emitted from the non-linear optical crystal for detection onto the array sensor; and a stage for placing the specimen, the stage being movable in at least one direction, wherein the wavelength-tunable far-infrared light source comprises: two near infrared light sources each having wavelengths different from each other; and a non-linear crystal onto which light oscillating from the near infrared light source is incident, the wavelength-tunable far-infrared light source being a light source that generates far-infrared light from a linear area by parametric generation, and the illumination optical system is an afocal optical system, that includes at least two optical elements, in which a rear focal plane of one of the optical elements matches with a front focal plane of another one of the optical elements, and that images far-infrared light emitting from the linear area of the wavelength-tunable far-infrared light source.

2. The far-infrared imaging apparatus according to claim 1, wherein one of the near infrared light sources irradiates a beam that passes through the non-linear crystal approximately in parallel to a side surface of the non-linear crystal, and the non-linear crystal includes a Si prism that extracts far-infrared light from the side surface.

3. The far-infrared imaging apparatus according to claim 1, wherein the far-infrared imaging optical system includes at least two lenses, and a side of the specimen of the far-infrared imaging optical system is a one-side object telecentric imaging optical system, or the far-infrared imaging optical system is a double telecentric imaging optical system.

4. The far-infrared imaging apparatus according to claim 3, wherein in a first cross section along the region on the line, the detection optical system images a portion around an emission surface of the non-linear optical crystal for detection on the array sensor.

5. The far-infrared imaging apparatus according to claim 4, wherein the detection optical system includes at least two lenses, and at least the detection non-linear optical crystal side of the detection optical system is telecentric in the first cross section.

6. The far-infrared imaging apparatus according to claim 3, wherein in a second cross section orthogonal to the region on the line, the detection optical system concentrates light emitted from the non-linear optic for detection on the array sensor.

7. The far-infrared imaging apparatus according to claim 6, wherein in the second cross section, the detection optical system images the portion around the emission surface of the non-linear optical crystal for detection on the array sensor.

* * * * *